United States Patent [19]
Hsu

[11] Patent Number: 5,148,807
[45] Date of Patent: Sep. 22, 1992

[54] NON-CONTACT TONOMETER

[75] Inventor: Hsiung Hsu, Columbus, Ohio

[73] Assignee: Ohio State University, Columbus, Ohio

[21] Appl. No.: 574,213

[22] Filed: Aug. 28, 1990

[51] Int. Cl.$^5$ .............................................. A61B 3/16
[52] U.S. Cl. ................................. 128/645; 128/648; 128/649
[58] Field of Search ............... 128/645, 646, 647, 649, 128/653, 660.02, 660.06, 661.02, 748, 774, 782; 73/524, 589, 605, 627

[56] References Cited

U.S. PATENT DOCUMENTS

| | | | |
|---|---|---|---|
| 3,763,696 | 10/1973 | Krakau | 128/645 |
| 3,948,248 | 4/1976 | Zuckerman et al. | 128/676 |
| 4,610,255 | 9/1986 | Shimura et al. | 128/660.7 |
| 4,819,649 | 4/1989 | Rogers et al. | 128/660.2 |
| 4,928,697 | 5/1990 | Hsu | 128/649 |

OTHER PUBLICATIONS

*Optics*, A. N. Matveev, Mir Publishers Moscow, 1988, pp. 189–205.
*Analog and Digital Communication Systems* Second Edition, Martin S. Roden, Prentice-Hall, 1985, Section 5.4 and 5.5.
*Communication Systems, An Introduction to Signals and Noise in Electrical Communication*, A. Bruce Carlson, McGraw-Hill Book Company, 1986, pp. 230–235.
*Electronic Communications Systems*, William D. Stanley, Reston Publishing Company, Inc. 1982, pp. 181–193.
"A Vibration Tonometer", C. E. T. Krakau, Ophthal. Res. 1:129–139 (1970).
"IOP Measurement Using Sonics and Coherent Optics," J. M. Hamelink, G. L. Cloud; Proceedings of the 29th Annual Conference on Engineering in Medicine and Biology 1976, Boston, MA, vol. 18, P7.13.
"IOP Measurement Using Sonic Excitation and Laser Velocimitry"; Dissertation for the Degree of Ph.D.; Michigan State University, Jack M. Hamelink 1978.
"Ocular Tonometry Through Sonic Excitation and Laser Doppler Velocimetry"; J. M. Hamelink, G. L. Cloud; Journal of Biomechanical Engineering, Nov. 1979 vol. 101/267–270.
"Non-Invasive Ocular Tonometry Using LDV," G. L. Cloud, D. C. Kanistanaux, J. M. Hamelink, PROC 1982 Joint Conference on Experimental Mechanics, Oahu--Maui, HI. May 23–28, 1982, pp. 322–326.

*Primary Examiner*—Randy C. Shay
*Attorney, Agent, or Firm*—Emch, Schaffer, Schaub & Porcello Co.

[57] ABSTRACT

A non-contact, non-invasive tonometer utilizing the technique of angle modulation of high frequency sound waves or high frequency light waves to determine the intraocular pressure of an eye. The angle modulation technique can be either frequency modulation or phase modulation.

15 Claims, 12 Drawing Sheets

NON-CONTACT TONOMETER

BACKGROUND OF THE INVENTION

The present invention is directed toward an improved tonometer system for use in the early detection of glaucoma. The tonometer of the present invention provides for an accurate measurement of intraocular pressure without making any physical contact with the eye and without need for eye drops or anesthetic. The tonometer of the present invention achieves these measurements through non-invasive and non-contact techniques. The tonometer of the present invention is related to and an improvement upon the tonometer which is described in my U.S. Pat. No. 4,928,697, which issued on May 29, 1990. The disclosures of my '697 patent are incorporated by reference herein.

Glaucoma is an eye disease which is one of the leading causes of blindness in the U.S. and throughout the world. Glaucoma is fairly common in adults over age 35. Two out of every one hundred persons in this age group have vision threatened by glaucoma.

When an object is viewed, the image is carried from the retina of the eye to the brain by the optic nerve. The optic nerve is an accumulation of over one million individual transmitters, each carrying a message to the brain. The individual messages all join together to provide side vision or peripheral vision as well as sharp central reading vision. Glaucoma can permanently damage the optic nerve, causing blind spots in areas of vision to develop. If glaucoma is undiagnosed, the optic nerve sustains considerable irreversible damage and may even be destroyed, resulting in blindness.

Glaucoma is detectable by measuring the intraocular pressure of the eye. Increased elevations of intraocular pressure are indicative of glaucoma situations or possible glaucoma situations. Intraocular fluid flows through the inner eye continuously to maintain the structure of the eye, in particular, the cornea. If the outflow or drainage system within the eye becomes blocked for any reason, the fluid backs up within the inner eye causing the fluid pressure to increase and thus causing damage to the optic nerve. The possibility of damage to the optic nerve increases with increasing pressure. The only preventative measure which can be taken is the early detection of glaucoma by periodic testing of the intraocular pressure since an elevated intraocular pressure is clearly basic to the whole concept of glaucoma.

A variety of mechanisms have been devised to facilitate the measurement of the intraocular pressure. The common available instrument, known as a tonometer, has the following general operational characteristics. The tonometer measures the force necessary to applanate or flatten a given area of the cornea. The measurement is directly related to the intraocular pressure because the cornea is flattened only when the external force equals the force applied by the ocular pressure plus the force necessary to deform the corneal tissue. The transition of the shape of the cornea from convex to planar can be detected by a simple optical principle. When a reflecting surface is illuminated with a narrow beam of light, the intensity of the reflected light gathered by a converging lens is maximal when the reflective surface is flat. Thus, if the cornea is illuminated by a narrow beam of light, the output of a photodetector placed at the focal plane of the lens will be maximal when the cornea flattens. Further, the flattened area should be ideally located at the apex of the cornea and perpendicular to the optical axis of the eye. This precaution is taken to minimize the deformation of the eyeball and to reduce the subsequent artifical increase of intraocular pressure due to the measurement. It should be noted however that the requirement of proper alignment is not always achieveable and some current tonometers have been designed to compensate for variations in the positioning of the measurement probe with respect to the optical axis of the eye. Finally, the last requirement for most currently available tonometers is that the application of the instrument on the eye be rapid and automatic.

There are an assortment of tonometers currently available which offer a variety of methods for measuring the intraocular pressure of the eye. The basic apparatus is the "Goldmann" applanation-type tonometer which is either hand held or designed for use as a fixed-type instrument. With the applanation-type tonometer, an applanating surface is placed in contact with the cornea and a force applied and varied until a fixed diameter of applanation of the cornea is achieved. The force of application is measured once the fixed diameter of applanation is achieved and this force is used to determine the intraocular pressure of the eye. The applanation-type tonometer must be used with a topical anesthetic. Another type of tonometer is the Schiotz-type or plunger-type tonometer. This tonometer is placed before the eye along the optical axis and a plunger is released which flattens the cornea to a specified diameter and measures the forces applied. Again, the Schiotz-type tonometer requires the use of a topical anesthetic. The Schiotz and Goldmann tonometers, while accurate in their measurement of intraocular pressure are quite undesirable to the patient in that they require the use of a topical anesthetic and further require that the eye be contacted by a mechanical device. Any contact with the corneal tissue carries the risk of infection and corneal abrasion. It also has been found that the patient usually has a somewhat high level of fear and physical discomfort as a result of such eye contact. Thus, the patient will tend to avoid the procedure, if possible.

Another consideration which is currently becoming a priority within the medical community is the desire to insulate the patient, physician and tonometer from mutual contact wherein bodily fluids may be communicated, whether by necessity or inadvertantly. The threat of contacting the Acquired Immune Deficiency Syndrome virus has created a new and desired objective of insulating the patient and eliminating, as much as possible, the need for any physical contact during examination.

A new generation of tonometers have been designed in an effort to limit contact with the eye which utilize an air puff pressure generation on the eye. The air puff system uses an air pulse generated from the ambiant atmosphere with a reliable positive linear force/time ramp. The air pulse impinges upon the cornea causing a gradual curvature reduction, applanation, and a finally slight concavity before the decaying force/time ramp permits restoration. Telecentric optical electronic monitoring of the corneal vertex reflection uniquely identifies, in time, the applanation event. This system has been described in detail in the American Journal of Optometry and Archives of the American Academy of Optometry, Vol. 49, August 1972, No. 8 "A new tonometer system", Grolman. While the air puff type tonometer has eliminated the need for the use of any form of topical anesthetic or the need for contact with the eye, the air puff tonometer creates an audible sound and sends a strong surge of air to the eye. Such sounds and air surges still have the possibility of causing physical or psychological discomfort in some patients.

It is an object of this invention to provide a tonometer which accurately measures the intraocular pressure without need for topical anesthetic and without any discomfort to the patient, whether psychological or physical.

It is another object of this invention to provide a tonometer which accurately measures the intraocular pressure through non-invasive and non-contact type techniques.

SUMMARY OF THE INVENTION

The present invention achieves the above objectives by providing a tonometer which utilizes the principles of angle modulation of high frequency waves which are directed toward the cornea. The angle modulation technique can be accomplished either through the techniques of frequency modulation or phase modulation. The high frequency waves are transmitted either as high frequency sonic waves or visible or invisible light waves.

The use of amplitude modulation of high frequency sound waves in tonometry has been fully explored in U.S. Pat. No. 4,928,697. The present invention which applies angle modulation techniques to tonometry offers a distinct alternative to the amplitude modulation techniques disclosed in may '697 patent. The hardware described in my '697 patent is similar to the hardware utilized in the present invention. However, the electronics incorporated for use with the hardware has been modified to utilize the techniques of angle modulation of high frequency sound or light waves. Therefore, if it is necessary to review hardware in order to develop a full understanding of the present invention, reference is hereby made to the '697 patent. However, the invention should be readily understood with reference to the accompanying drawings and the detailed description of those drawings which follows.

BRIEF DESCRIPTION OF THE DRAWINGS

FIG. 4a is a circuit diagram for the low frequency oscillator A of FIGS. 3 and 3a.

FIG. 4b is a circuit diagram for the high frequency oscillator B of FIGS. 3 and 3a.

FIGS. 4c and 4e are circuit diagrams for the remaining components of the tonometer of FIG. 3a.

DETAILED DESCRIPTION OF THE INVENTION

The present invention utilizes the principles of angle modulation to accurately determine the intraocular pressure of an eye. In my previous patent, I used amplitude modulation of a high frequency sound to determine the intraocular pressure. In the '697 patent, the amplitude of the high frequency signal was varied by a low frequency perturbating sound wave and the variation in the amplitude was then processed to correlate with the intraocular pressure of the eye. In contrast, the present invention utilizes the technique of angle-modulation of high frequency signals. The angle of the high frequency sound or light wave is varied in accordance with a low frequency pertubating acoustic wave. Angle modulation is defined as a process in which the angle of a sinusoidal reference function is varied in accordance with the modulating signal. The two forms of angle modulation that are utilized in the present invention are phase modulation and frequency modulation. The general forms of the phase modulation (PM) and the frequency modulation (FM) signals differ only in the relationship of the angle variation to the modulating signal. Frequency modulation (FM) signals are dependent upon velocity changes or the time rate of change of the phase of the signal. Phase modulation (PM) signals are dependent upon path differences (i.e., spatial changes). As a result of the interrelationship between FM and PM, the present invention can be utilized with either the phase modulation or frequency modulation techniques of angle modulation.

Figure 2:
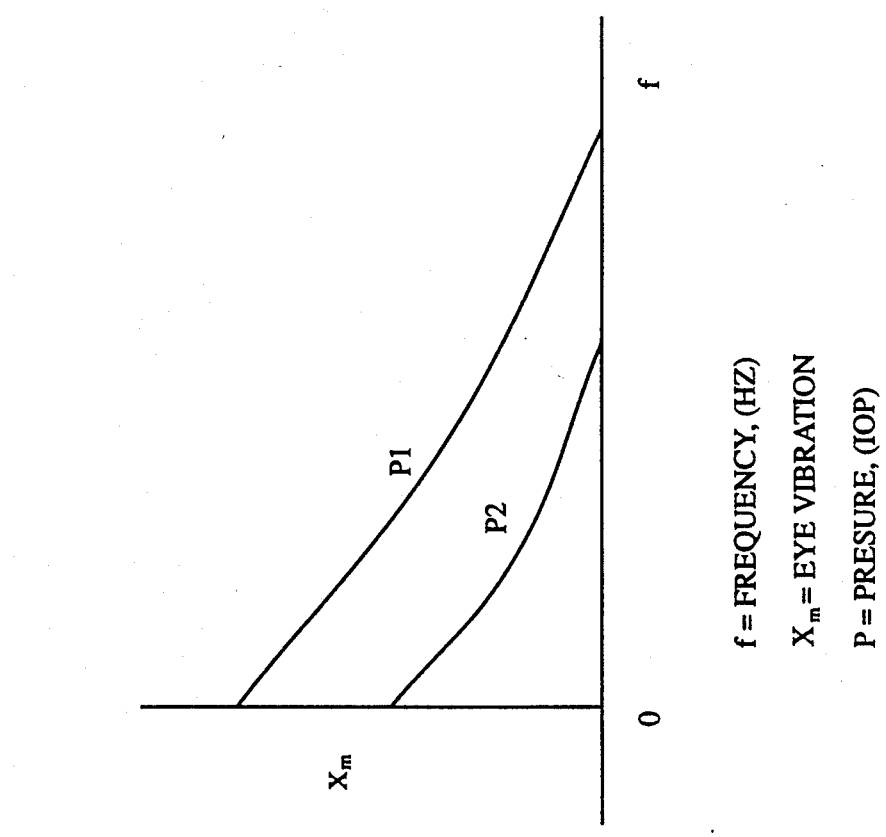
FIG. 2 is a representation plotting the displacement of the corneal surface by an acoustic vibration against increasing frequencies for two distinct and constant intraocular pressures.
Figure 1:
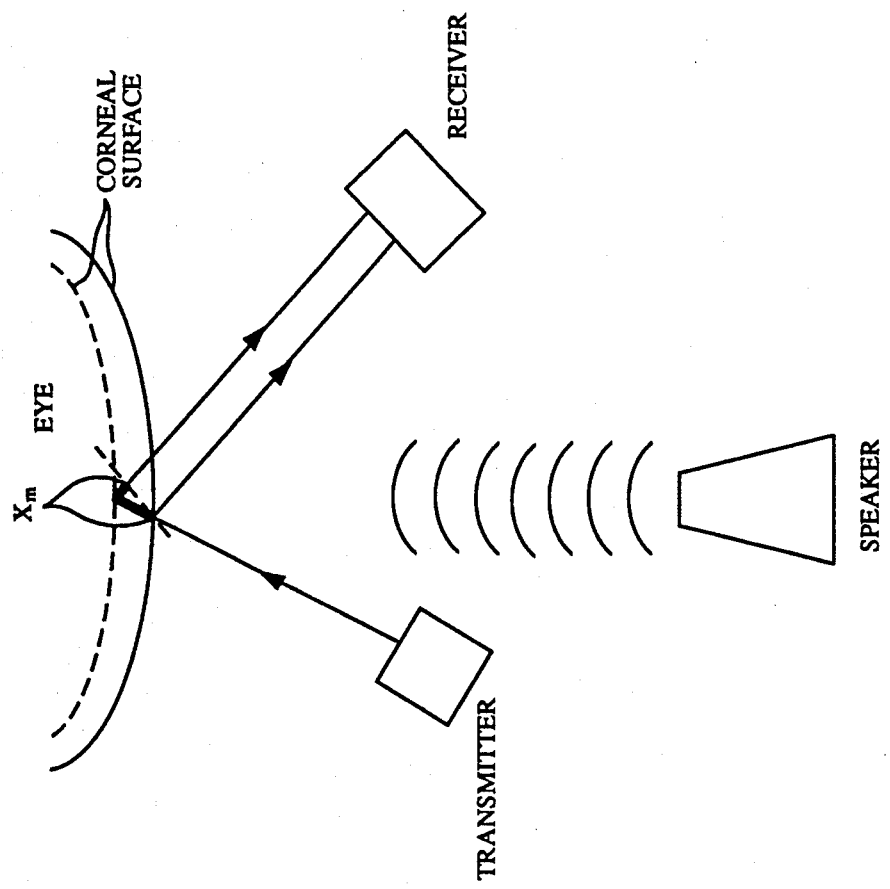
FIG. 1 is a schematic representation of the reflective paths followed by high frequency sound for two extreme situations corresponding to the limits of the vibration of the corneal surface due to a low frequency acoustic excitation.

The principle behind the present invention is understood by reference to FIGS. 1 and 2. A low frequency sound wave is transmitted toward the eye from the speaker. The low frequency wave is preferably generated in the range of 10-500 Hz. The low frequency sound wave causes an acoustic vibration of the corneal surface of the eye. The amplitude of the acoustic vibration is generally dependent upon the intraocular pressure (IOP) of the eye as well as the frequency of the sound wave. The corneal vibration initiated by the low frequency perturbating sound wave is generally sinusoidal in nature. There may be some inherent distortions of the vibration created by harmonics and other factors such as the pulmonary pulse registered through the corneal surface. These potential distortions will dictate the design of the electrical circuitry to be utilized with the FM and PM embodiments of the present invention.

Referring again to FIG. 1, the path of the high frequency sound signal originating from the transmitter is shown for two extreme situations corresponding to the limits of the acoustic vibration of the corneal surface due to the low frequency excitation. There is a difference ($X_m$) in path length of the high frequency wave which is shown in FIG. 1 in the darkened portion of the wave paths between the two positions of the corneal surface. If Xm is the maximum difference in the path length shown in FIG. 1, then the actual path difference versus time can be expressed as:

$$X(t) = Xm \sin(\omega t)$$

where $\omega$ is the angular frequency of the low frequency signal. The effect of the actual path difference versus time X(t) on the high frequency signal transmission from the transmitter to the receiver is to cause a phase delay in the high frequency signal. There will be a phase delay of 360° if X(t) reaches the value of the wavelength of the high frequency signal. Thus, the received high frequency signal is phase modulated with a phase angle $\theta$ (t) which is dependent upon the low frequency acoustic signal as:

$$\theta(t) = 360° \cdot Xm \sin(\omega t)/\lambda$$

where, $\lambda$ is the wavelength of the high frequency signal.

Since the path difference (Xm) is a known function of the low frequency acoustic signal and intraocular pressure, the value of intraocular pressure can be measured by phase demodulation techniques. Because, the output of the tonometer is specifically at the angular frequency ($\omega$) of the low frequency acoustic signal, all other possible noise and interference outside of the range of the low frequency acoustic signal can be filtered to provide variable band width control of the signal as desired.

When using phase modulation techniques, two waves of the same frequency are superimposed or added together and the resulting wave will be enhanced in amplitude where the two phases are identical and will be reduced in amplitude where the two phases are opposite (i.e., 180° apart). If the relative phase between the two waves is varied, e.g., by delaying one wave with respect to the other, the relative phase will change by 360° for every delay of one wavelength. Consequently, by monitoring the relative phase differences between two waves, the difference in their path lengths can be calculated. When using high frequency waves or any electromagnetic waves, the resulting phase difference and thus, the resulting path difference can be then electronically displayed on an oscilloscope. The phase difference can also be electronically displayed through the use of phase locked loop demodulation techniques. When using optical waves, the phase difference and thus, the path differences can be easily observed through the use of interferometers which provide a display of interference fringes for the enhancement or reduction of the resulting wave. Since each interference fringe indicates a difference of 360° in phase or the path difference of one wavelength, it should be remembered that the phase difference is directly proportional to the path difference in terms of wavelength.

Referring now to FIG. 2, the amplitude of the acoustic vibration of the cornea is shown to have an inverse relationship to the intraocular pressure as well as the frequency of the perturbation or acoustic vibration. For a fixed pressure inside the eye, the amplitude of the acoustic disturbance corresponding to the path difference $X_m$ decays as the frequency increases. This leads to the physical interpretation that the eye can be pushed in by a steady force, i.e., a finite $X_m$, with a frequency of 0. At high frequencies, the eye no longer follows the acoustic vibration and $X_m$ eventually decays to 0. When the intraocular pressure is raised, the amplitude of the acoustic vibration is reduced for the same sound wave intensity. Thus, the curve is lower for higher intraocular pressures. It is seen, when the frequency of the acoustic sound wave is fixed, there is a direct relationship between the intraocular pressure and the path difference $X_m$ which is measured from the phase difference. The information contained in the graph of FIG. 2 is ultimately utilized to correlate the output readings of the tonometer to known measurements of intraocular pressure. The graph, in working form will contain a variety of curves corresponding to $X_m$ and frequency at varying intraocular pressures. In order to calibrate $X_m$ with intraocular pressure, the graph of FIG. 2 can be altered to provide the values of $X_m$ against the intraocular pressure for a given constant frequency. Thus, for any given frequency and value of $X_m$, the reading for the intraocular pressure can be obtained.

The calibration graph is produced through the use of the present invention with an artificial eye in which variable amounts of known pressure can be provided. By keeping a constant known pressure within the eye and varying the frequency of the perturbating acoustic wave, the corresponding values of $X_m$ can be obtained.

To calibrate the tonometer, the frequency of the perturbating acoustic wave is kept constant while the intraocular pressure within the artificial eye is altered. The values of $X_m$ for varying pressures can then be plotted and used to correlate the values of $X_m$ obtained during actual tonometer use to actual readings of intraocular pressure.

Figure 3:
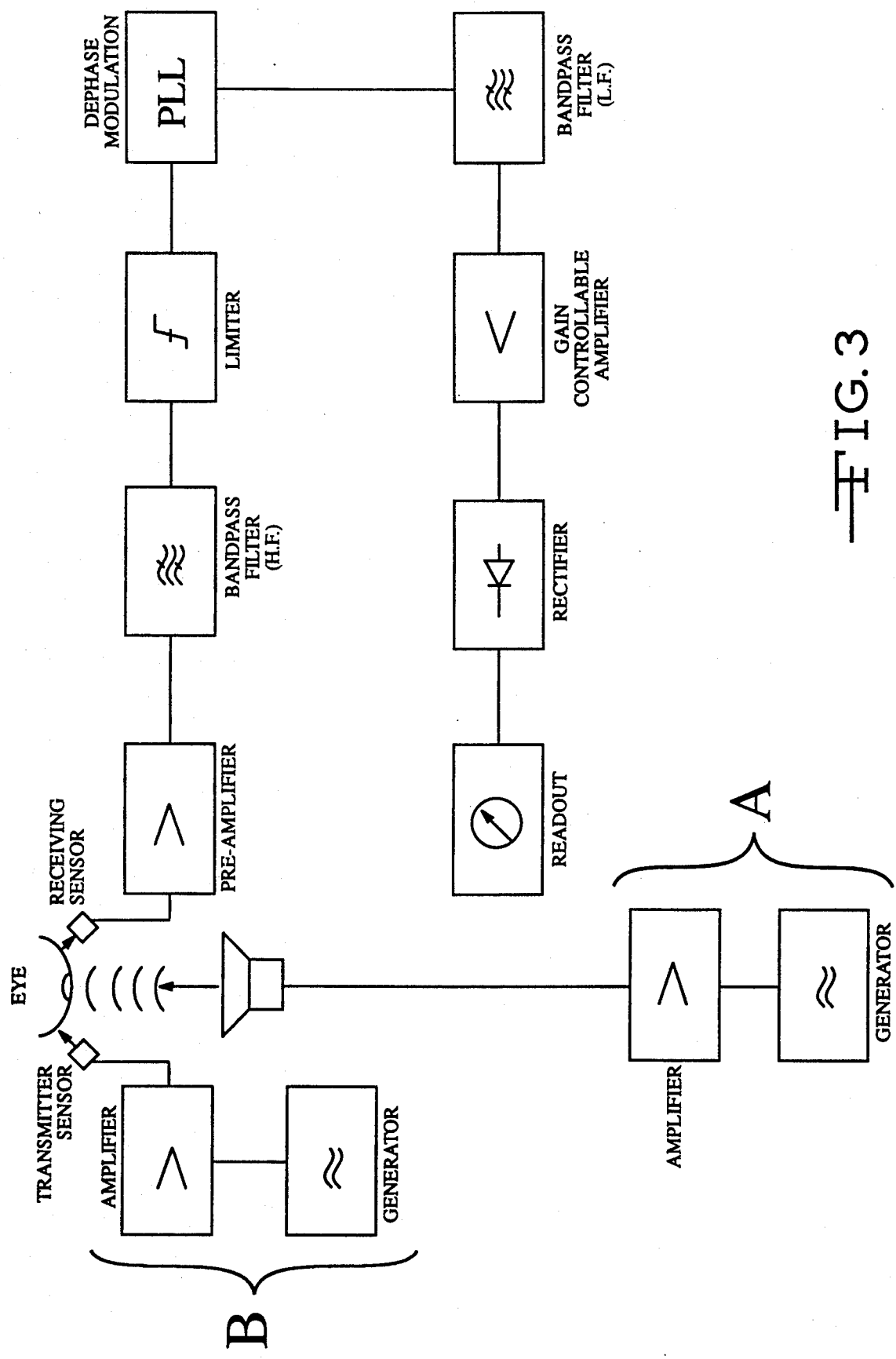
FIG. 3 is a block diagram for the frequency modulation tonometer of the present invention.
Figure 3A:
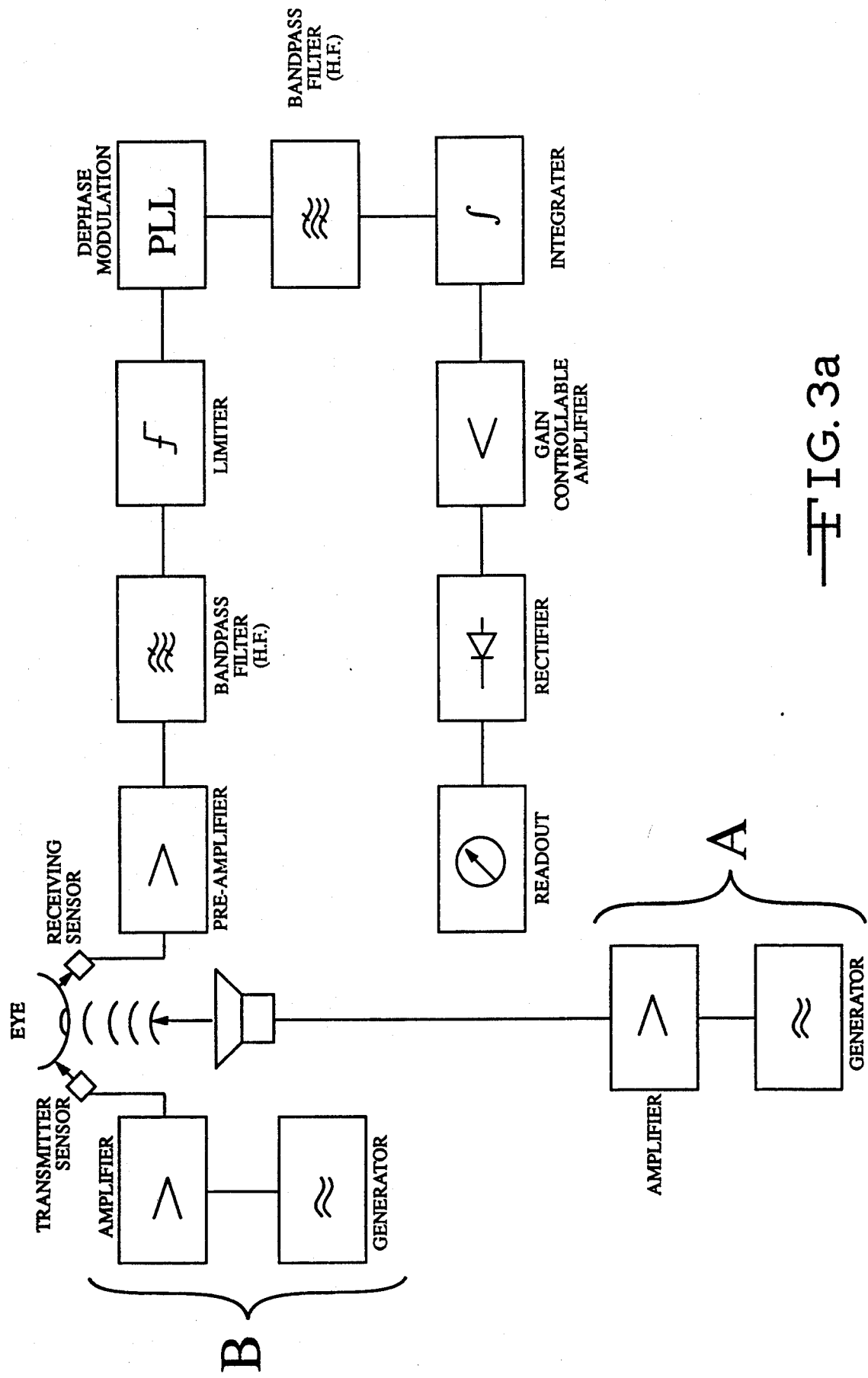
FIG. 3a is a block diagram for the phase modulation tonometer of the present invention.
Figure 4A:
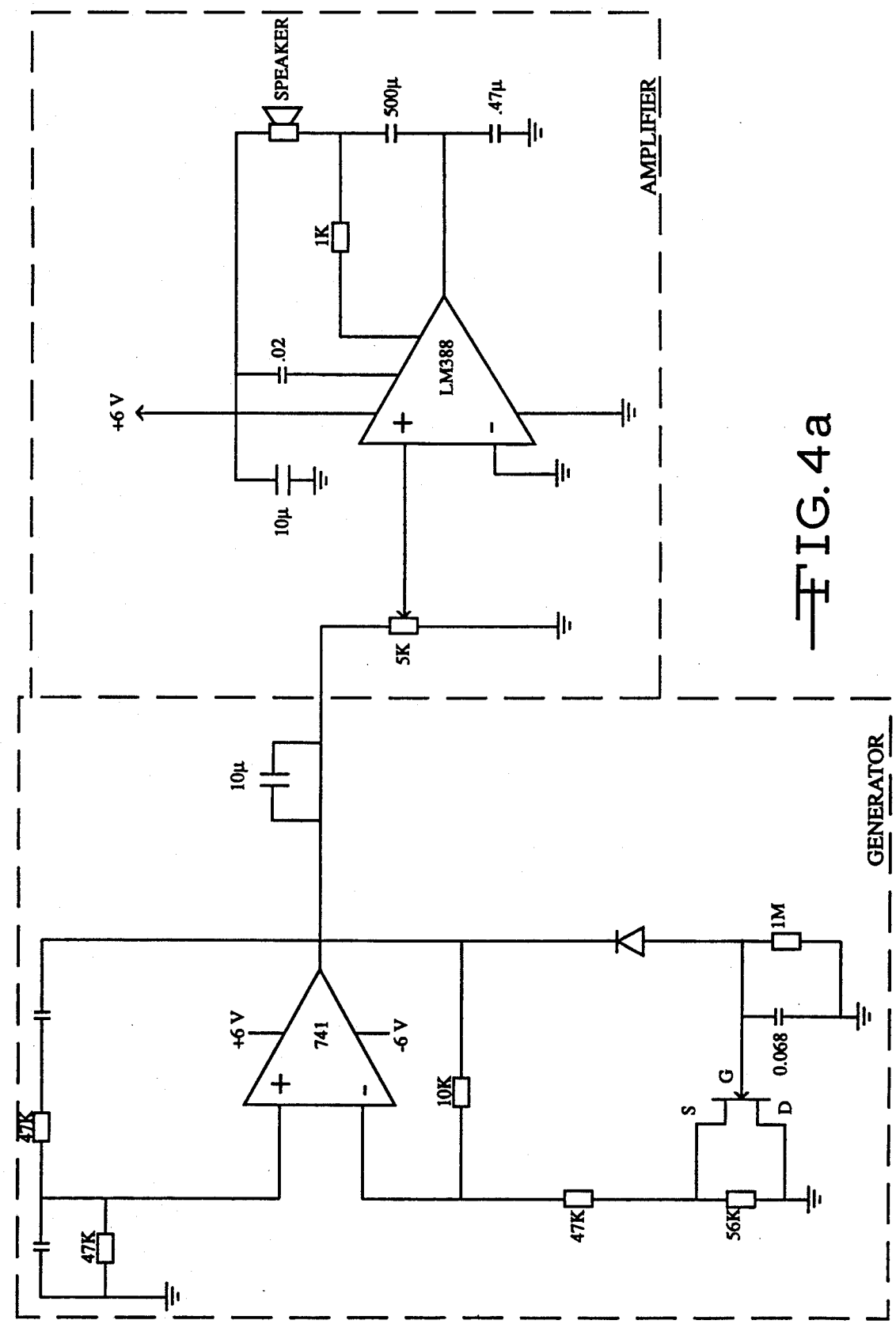
Figure 4B:
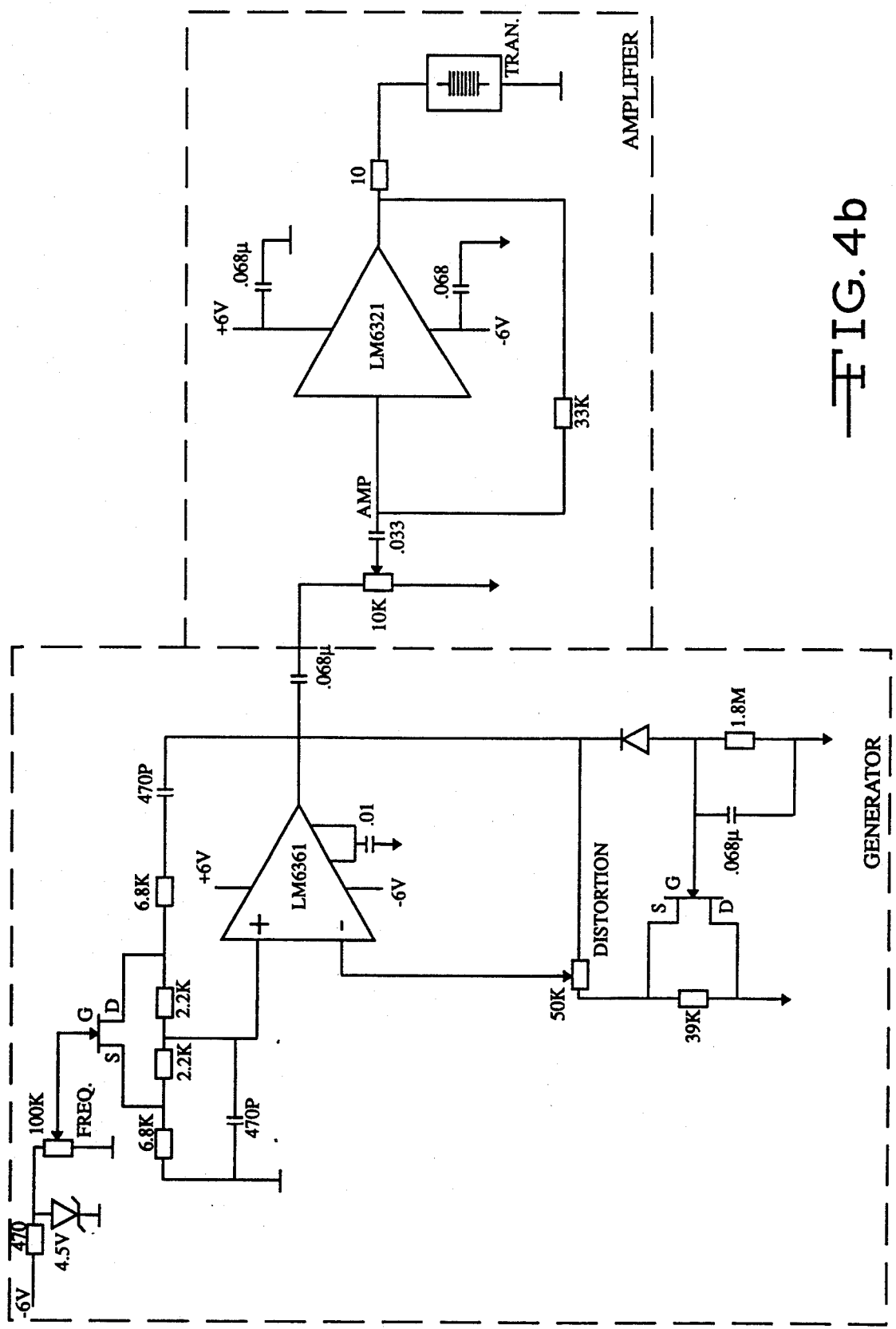
Figure 4C:
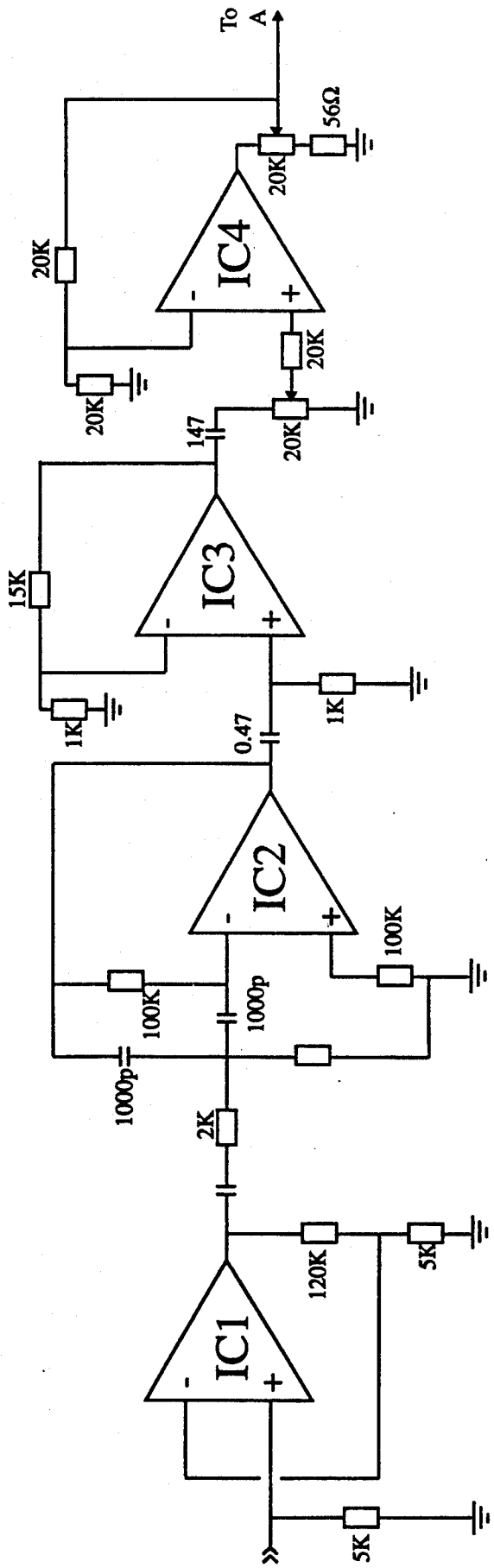
FIGS. 4c and 4d are circuit diagrams for the remaining components of the tonometer of FIG. 3.
Figure 4D:
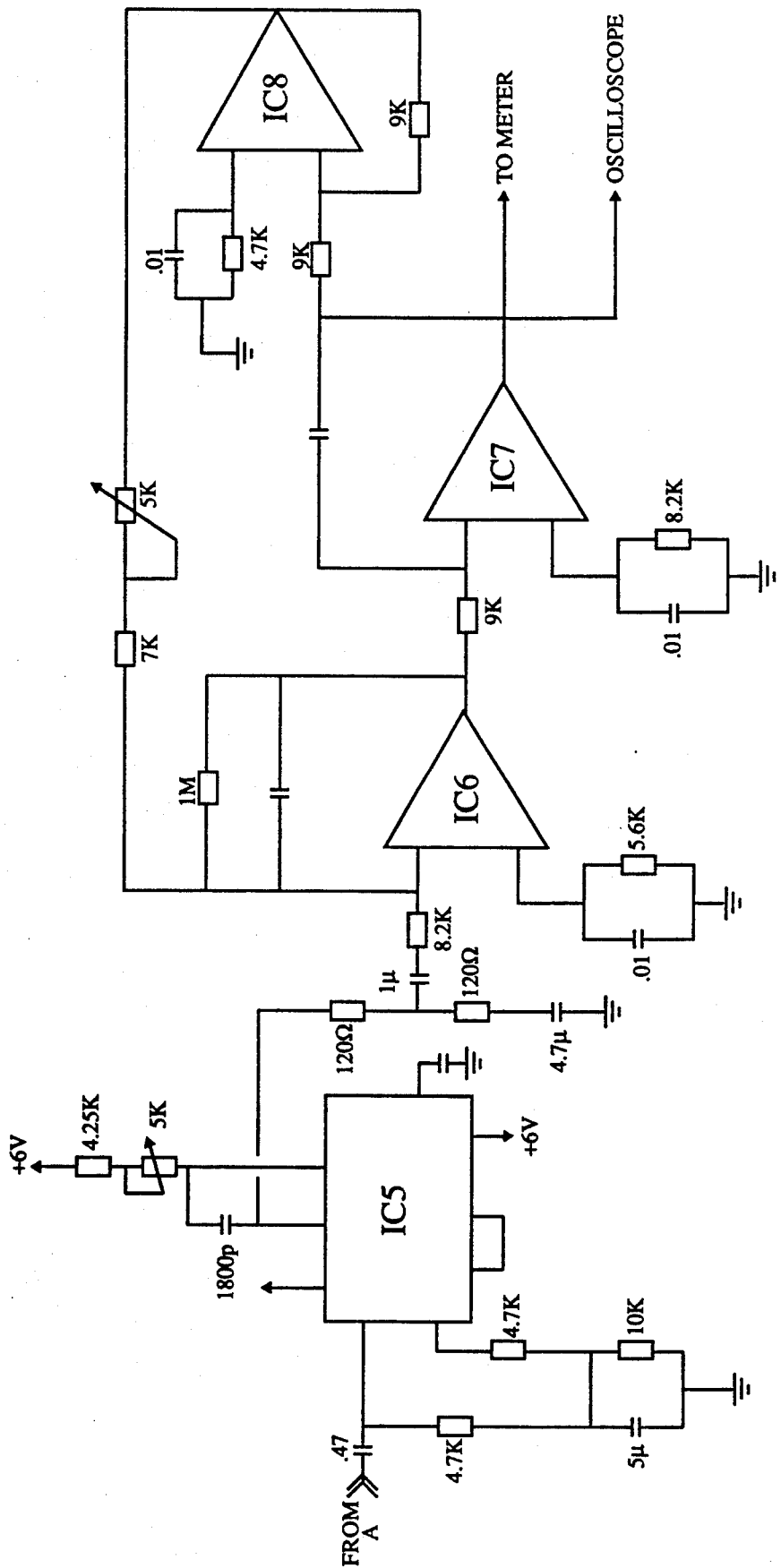
Figure 4E:
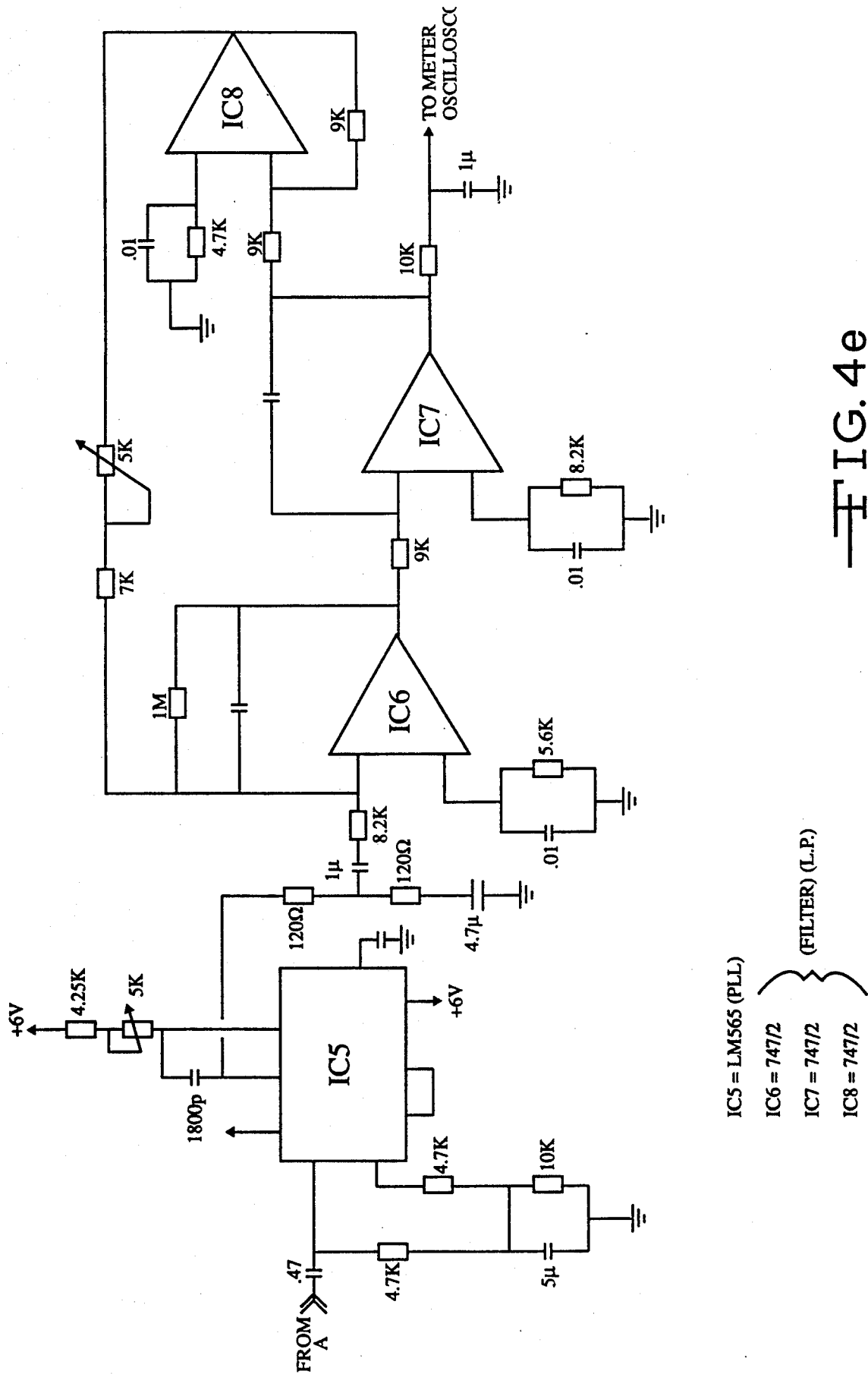

Referring to FIG. 3 and the accompanying FIGS. 4a, 4b, 4c and 4d, the circuits of the tonometer utilizing frequency modulation of a high frequency sound wave are shown. Referring to FIG. 3a and 4a, 4b, 4c and 4e, the circuits of the tonometer utilizing phase modulation of a high frequency sound wave are shown. A comparison of FIG. 3 with FIG. 3a will provide an understanding of the distinctions between frequency modulation and phase modulation. FIG. 3 is a circuit designed to detect frequency modulation which is dependent upon velocity change which is the differential of displacement. Displacement, then is the integration of velocity. Thus, FIG. 3a is the same circuit as FIG. 3 with the addition of an integrator circuit. The addition of an integrator circuit to an FM circuit thereby provides a PM circuit. Referring to FIG. 4e, it is seen that the integrator circuit is a combination of a 10K resistor and 1 microfaraday ($\mu$) located proximate the output terminal.

In practice, the interchangability of the FM and PM circuits allows for great flexibility in designing the operational characteristics of the tonometer of the present invention. Usually the PM detector circuit will provide data relating the true performance of the intraocular pressure over time. However, if the PM display indicates an abnormality for the patient, the readout can easily be switched to provide FM data which will observe the time rate change of the abnormality and possibly provide easier detection of the symptoms.

The tonometer, utilizing either FM or PM, generally operates as follows. A low frequency perturbating sound wave, generally between 10–500 Hz, is provided via a generator and amplifier (oscillator A) to the speaker. The perturbating sound wave is used to vibrate the corneal surface; the displacement of the vibration of the corneal surface being directly related to the intraocular pressure of the eye. A high frequency sound wave, generally between 10 KHz and 1 MHz, is initiated via a second generator and amplifier (oscillator B) to a transmittor. The high frequency sound wave reflects off of the corneal surface as shown in FIG. 1 and is received by the sensor. The modulation signal received by the sensor is of a very small voltage, usually microvolts. Therefore, it is forwarded to a preamplifier which enlarges the small signal to a signal of milivolts or volts thereby allowing for processing of the signal. The modulated signal is then passed through a high frequency bandpass filter (H. F.) which is used to pass the high frequency signal as modulated at the frequency of the perturbating sound wave and eliminate all unwanted high frequency noise. For instance, if the high frequency sound wave is operated at the frequency of 40 KHz, the bypass filter will be a 40 KHz filter which allow only a modulated signal of 40 KHz to pass through. The filtered and modulated high frequency signal is then processed by a limitor circuit which eliminates any amplitude fluctuations of the signal and provides for easier processing. The limitor circuit will, in effect, keep all the signals at the same strength and allow for the improvement of the signal to noise ratios through the incorporation of appropriate filters.

The modulating high frequency signal is then processed by a phase locked loop circuit (PLL) to dephase the modulation. The phase locked loop circuit tracks the input modulated phase and its output indicates the amount of phase shift from the original input from the oscillator B. Phase locked loop circuits are a feedback circuit used to demodulate angle modulated wave forms. The phase locked loop circuit incorporates a voltage controlled oscillator in the feedback loop whose output frequency is a function of its input voltage. The output from the phase locked loop circuit is then fed to a low frequency bandpass filter intended to eliminate any low frequency noise outside the range of the original low frequency (oscillator A) signal. For instance, if the low frequency (oscillator A) signal is at 200 Hz, the low frequency bandpass filter eliminates any signals outside the 200 Hz range. Referring then to FIGS. 3 and 3a, the output from the low frequency bandpass filter is then integrated if phase modulation is desired or it is passed directly to the remaining circuits if frequency modulation is desired. The remaining circuits, the gain controllable amplifier and the rectifier, provide final cleansing of the signal output for display on the readout which is usually a meter or an oscilloscope.

Figure 5:
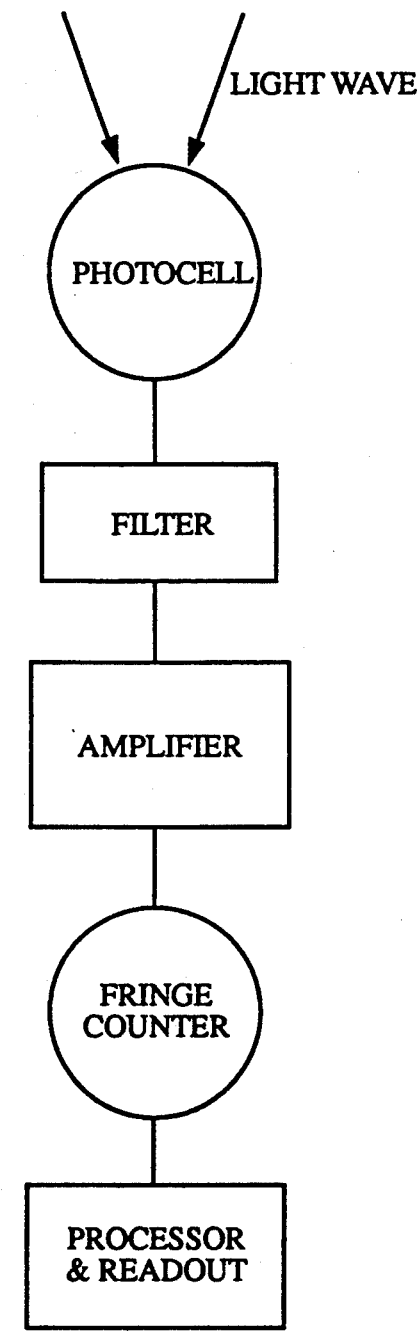
FIG. 5 is a block diagram representing the optical interferometer embodiment using phase modulation of the present invention.

An alternative embodiment of the present invention is to utilize the angle modulation techniques described above to modulate light waves directed toward the corneal surface and process the signals to provide information related to intraocular pressure. Referring now to FIG. 5, the schematic block diagram shows the use of a photocell to detect and receive phase modulated light wave signals from the acoustically vibrating corneal surface as well as a reference signal from an optical interferometer. The circuit of FIG. 5 can also be modified, through the addition of a differentiator, not shown, to provide for frequency modulation detection, if it is so desired. The photocell collects these signals and processes them through a filter to eliminate unwanted noise then amplifies the signals for projection into a fringe counter. The signal from the fringe counter is then provided to the processor for processing into a readable form which is indicative of the intraocular pressure of the eye.

The intensity of the wave which is received by the photocell and processed through the fringe counter results from the superpositioning of two distinct light waves and is determined by the merger between their distinct phases and polarizations. The interference fringe pattern is generally produced by combining two monochromatic waves of identical frequency. Waves suitable for this purpose are obtained as a result of the division of the same wave into two parts. The present invention utilizes an amplitude division of a light wave to produce the interference fringe pattern.

Figure 9:
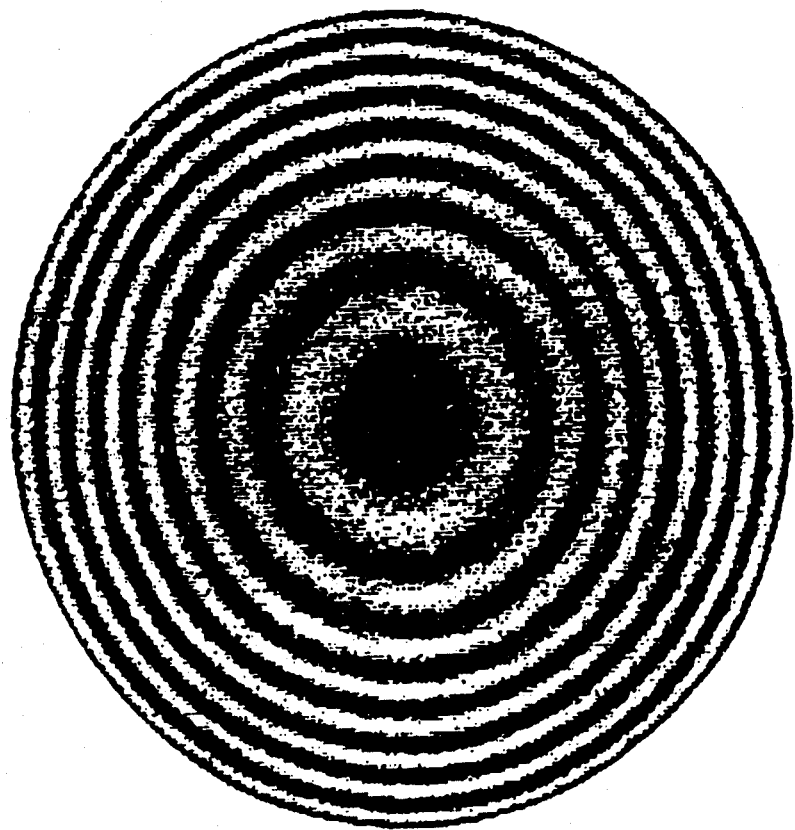
FIG. 9 is a representation of the fringe interference pattern which appears through the use of a Michaelson or Mach Zehnder-type interferometer.

The photocell is positioned to intercept a portion of the fringe pattern, a sample of which is shown in FIG. 9. Preferably, the photocell is positioned to accept input from the center of the fringe pattern. As the cornea is acoustically vibrated by the low frequency perturbating sound, the fringe pattern will shift or move as if new fringes are created at the center of the pattern and flow outwardly during one cycle of the vibration and then reverse and flow inwardly during the opposite cycle of the vibration. As the fringes move, the photocell registers pulses, each pulse indicative of the passage of one fringe. The fringe counter will count the number of pulses against time and the resulting value is correlated to $X_m$ since each fringe is the equivalent of a displacement of one wavelength in $X_m$. Thus, a graph similar to FIG. 2 can be plotted using the number of fringes or pulses counted as the data for $X_m$. The calibration curve for the intraocular pressure can then be plotted for a constant frequency.

Figure 7:
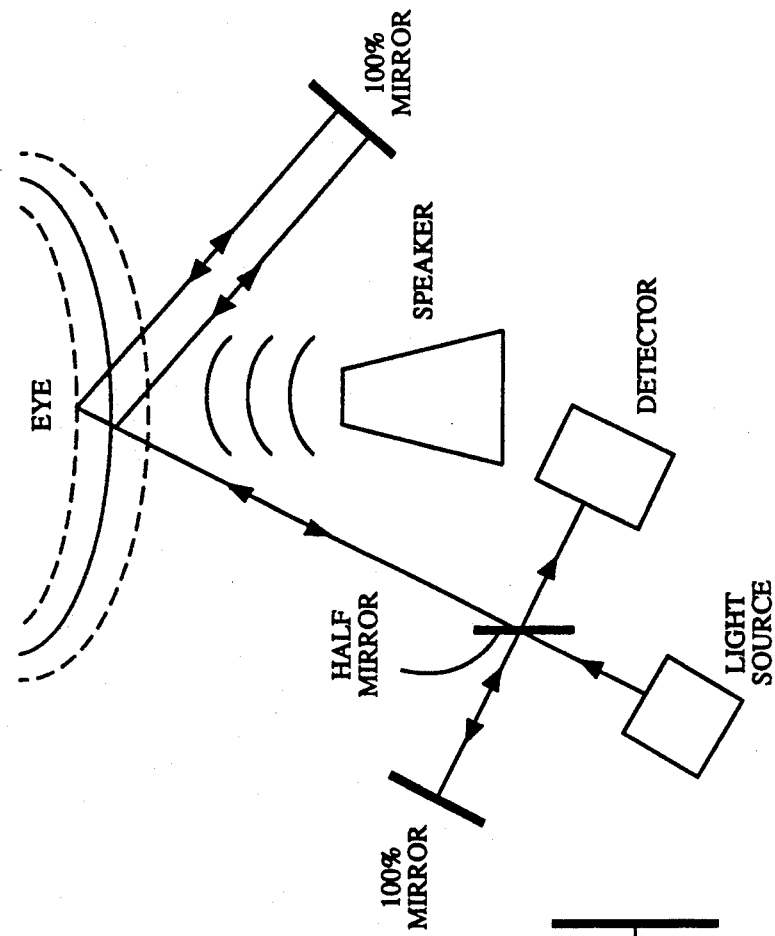
FIG. 7 is a schematic representation of an alternative embodiment utilizing a Michaelson-type interferometer with the invention of FIG. 5.
Figure 6:
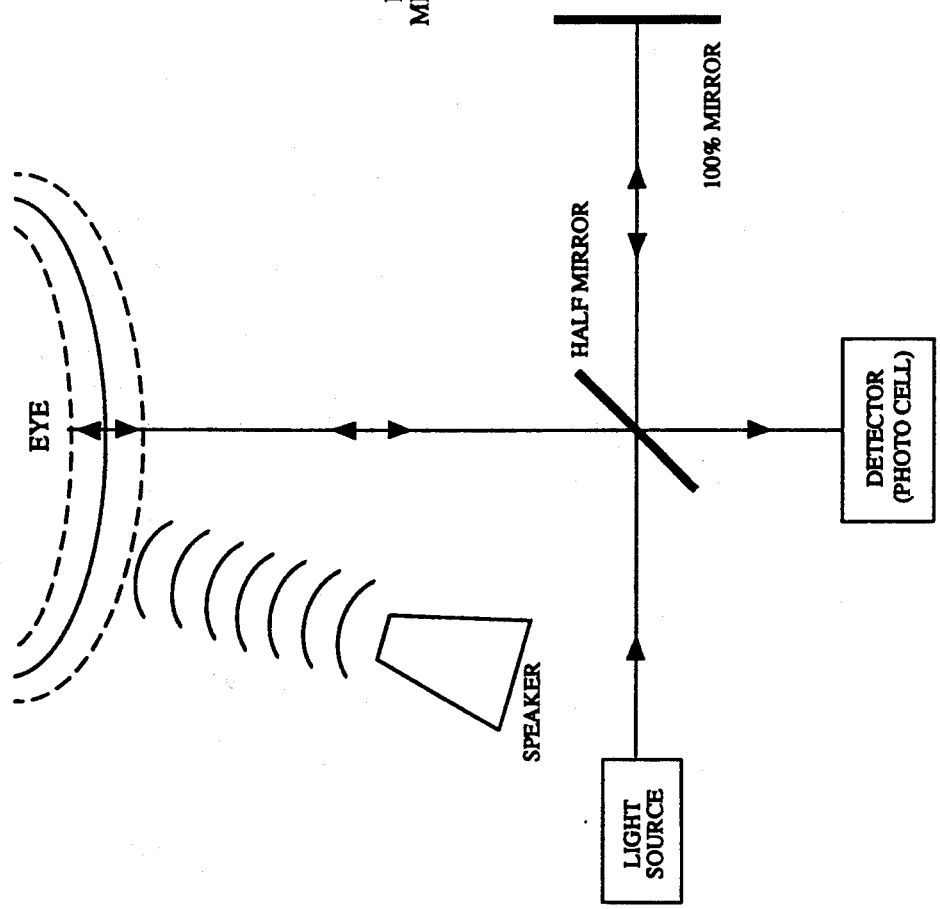
FIG. 6 is a schematic representation of the incorporation of a Michaelson-type interferometer with the invention of FIG. 5.
Figure 8:
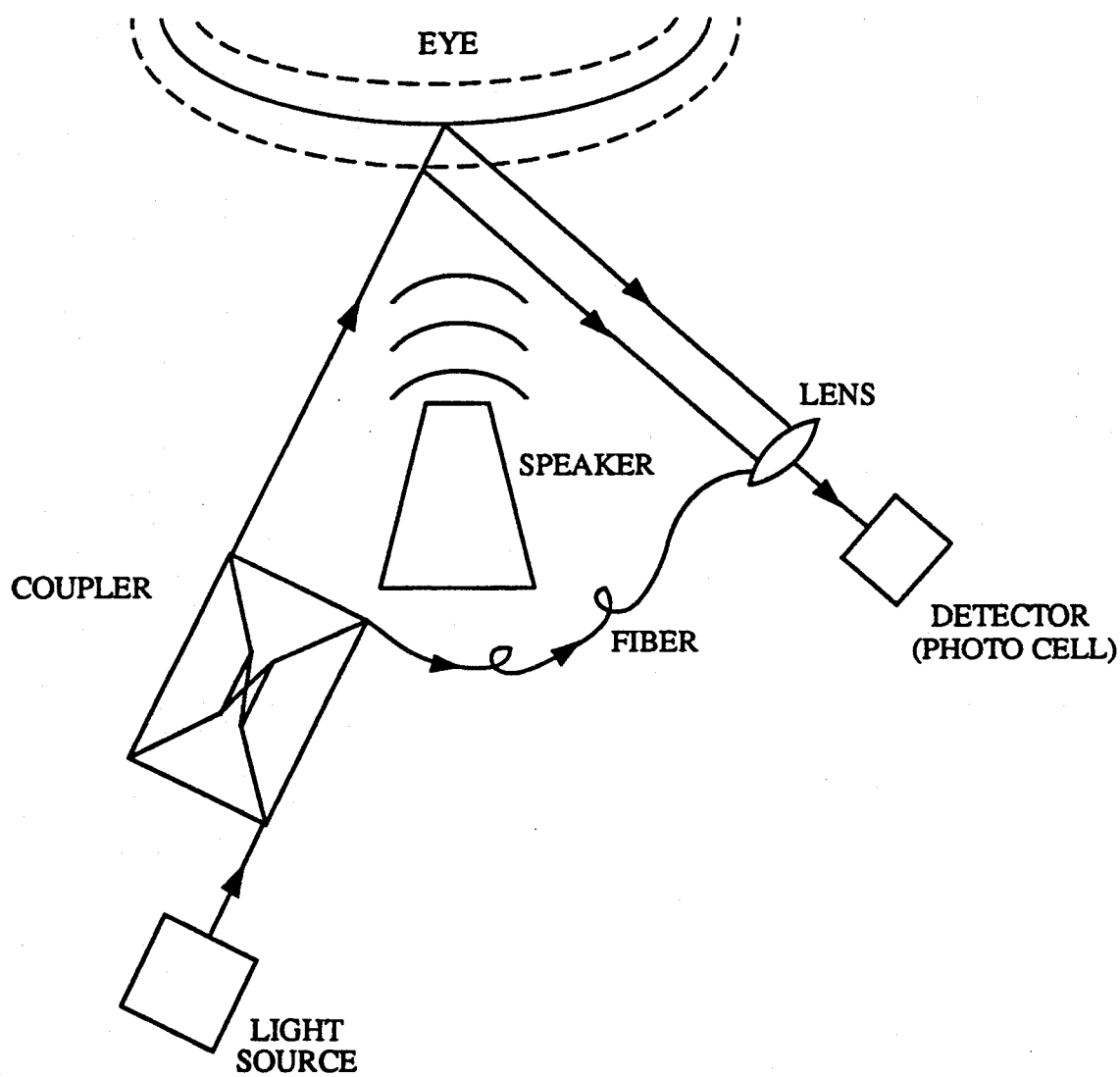
FIG. 8 is a schematic representation of the incorporation of a Mach Zehnder-type interferometer with the invention of FIG. 5.

Referring now to FIGS. 6, 7 and 8, various embodiments of the present invention are shown. FIG. 6 shows the incorporation of a Michaelson interferometer into the present invention to provide the reflected and modulated light wave to the photocell of FIG. 5. The corneal surface of the eye is again acoustically disturbed by the low frequency perturbating sound waves produced by the speaker. The sound waves are in the range of 10 to 500 Hz. A coherent beam of light from a light source, such as a low-power laser or light-emitting diode, is projected onto a half mirror which evenly splits the beam of light, directing 50% toward a whole mirror and the remaining 50% toward the eye. The modulating corneal surface of the eye reflects the light beam in a modulated pattern back toward the half mirror and the whole mirror also reflects the light beam toward the half mirror. The half mirror, upon receiving both reflected beams, combines the beams and submits them to the photocell for processing. The modulating pattern of the light wave reflecting off of the acoustically distrubed corneal surface will be out of phase with the remaining 50% of the original beam when the two split beams are combined or merged at the half mirror and directed toward the photocell. Since there is a disruption in the phases of the merged light waves, an interference pattern, such as that shown in FIG. 9 will be produced.

Referring now to FIG. 7, the Michaelson interferometer is shown in an alternative orientation to the corneal surface. In this embodiment, the light source is angularly disposed with respect to the corneal surface. A second whole mirror is positioned adjacent the corneal surface to receive the modulated light wave reflected off the corneal surface. The second whole mirror reflects the modulated light wave to effect its return to the half mirror for combination with the remaining half beam and direction toward the photocell.

FIG. 8 shows yet another embodiment of the present invention utilizing a Mach Zehnder interferometer wherein the light source transmits a beam of light to a light coupler which splits the beam of light into two equal beams. One of the split beams is directed toward the acoustically modulating corneal surface of the eye and the remaining split beam is sent via an optic fiber directly to a focusing lens. The beam directed toward the modulating corneal surface of the eye is acoustically disturbed upon reflection and the acoustically distrubed beam is reflected to the focusing lens. The focusing lens receives the two distinct rays and combines them together for transmission to the photocell. Since one beam remains unmodulated and the reflected beam is acoustically disturbed, they will be out of phase and an interference pattern will be created. Again, the interference fringe can then be processed to calculate the intraocular pressures.

In the preferred embodiment of this invention, whether using sound waves or light waves for the high frequency source, the low frequency acoustic wave transmitted by the speaker and the high frequency wave transmitted by the transmitter are pulsed to prevent interference between the low frequency perturbating wave and the high frequency transmission. As the low frequency wave is propagated from the speaker towards the eye, the density of the air is also modulated by the low frequency sound. Thus, when the high frequency wave passes through the modulating medium, the high frequency propagation may be perturbed by the low frequency modulating medium resulting in undesirable fluctuations in the detected signal of the tonometer. This undesirable interference is easily eliminated by using a pulsed signal for the low frequency perturbating sound. The cornea of the eye will essentially still vibrate at the low frequency acoustic perturbation due to the pulsed low frequency excitation. But, for most of the time, when the pulse is no longer present, there will be no low frequency sound to create the undesirable interference. The receiver can then be programmed to detect and process the high frequency signals only during the time interval the low frequency pulse is absent. This will eliminate any unwanted low frequency interferences of the high frequency pulse.

The above description of the preferred embodiment of the present invention is intended to be illustrative of the invention as a whole. It is not intended to be limiting upon the scope and content of the following claims.

I claim:

1. A tonometer for use in the non-contact measurement of intraocular pressure of an eye comprising, in combination:
    means for producing a low frequency perturbating acoustic wave adapted to be positioned proximate a fixed eye wherein such perturbating acoustic wave is directed toward the eye for causing a vibration on the surface of the eye, the intensity of the vibration being dependent upon the intraocular pressure;
    means for transmitting a high frequency wave adapted to be positioned proximate said perturbating wave producing means and the eye, such high frequency wave being transmitted toward the eye for reflection off the perturbated surface of the eye;
    means for receiving such reflected high frequency wave and for detecting any modulation in the phase angle of such high frequency wave created by the acoustic vibration of the surface of the eye;
    means for creating an output signal based upon such phase angle modulation; and
    means for displaying such output signal for viewing.

2. the tonometer of claim 1, wherein said means for producing a low frequency perturbating acoustic wave operates in a range between 10 Hz and 500 Hz.

3. The tonometer of claim 1, wherein said means for transmitting a high frequency wave operates in a range between 10 KHz and 1 MHz.

4. The tonometer of claim 1, wherein said means for detecting any modulation in the phase angle of such high frequency wave includes a phase lock loop circuit for calculating the path difference between such high frequency wave being transmitted toward the eye and such high frequency wave being reflected off the perturbated surface of the eye.

5. The tonometer of claim 1, wherein said means for producing a low frequency perturbating acoustic wave includes a means for pulsing such wave such that the surface of the eye will perturbate at a desired frequency without receiving continuous stimulation from such low frequency wave.

6. The tonometer of claim 5, wherein said means for transmitting a high frequency wave includes a means for pulsing such high frequency wave such that such high frequency wave is transmitted toward the eye and the reflected wave is received from the eye during the period when the low frequency perturbating wave is pulsed off and not directed toward the eye.

7. The tonometer of claim 1, wherein said means for detecting any modulation in the phase angle of such high frequency wave includes a filter means having a variable band width control for eliminating any noise and interference in the signal that may be produced by the low frequency perturbating acoustic wave while maintaining any other desirable fluctuations in such signal.

8. A tonometer for use in the non-contact measurement of intraocular pressure of an eye comprising, in combination:
    means for producing a low frequency perturbating acoustic wave adapted to be positioned proximate a fixed eye wherein such perturbating acoustic wave is directed toward the eye for causing a vibration on the surface of the eye, the intensity of the vibration being dependent upon the intraocular pressure;
    means for transmitting a high frequency wave adapted to be positioned proximate said perturbating wave producing means and the eye, such high frequency wave being transmitted toward the eye for reflection off the perturbated surface of the eye;
    means for receiving such reflected high frequency wave and detecting any modulation in the frequency of such high frequency wave created by the acoustic vibration of the surface of such eye;
    means for creating an output signal based upon such modulation; and
    means for displaying such signal for viewing.

9. The tonometer of claim 8, wherein said means for producing a low frequency perturbating acoustic wave operates in a range between 10 Hz and 500 Hz.

10. The tonometer of claim 8, wherein said means for transmitting a high frequency wave operates in a range between 10 KHz and 1 MHz.

11. The tonometer of claim 8 wherein said means for detecting any modulation in the frequency of such high frequency wave includes a means for determining the time rate of change of the phase of such reflected wave from the phase of such transmitted wave.

12. A tonometer for use in the non-contact measurement of intraocular pressure of an eye comprising, in combination:

means for producing a low frequency perturbating acoustic wave adapted to be positioned proximate a fixed eye wherein such perturbating acoustic wave is directed toward the eye for causing a vibration on the surface of the eye, the intensity of the vibration being dependent upon the intraocular pressure;

means for transmitting a light wave adapted to be positioned proximate said perturbating wave producing means and such eye; wave splitting means for receiving such transmitted light wave and producing therefrom a first light wave and a second light wave of equal phase;

means for transmitting such first light wave toward the eye for reflection off such perturbated surface of the eye, such first light wave developing a variable phase delay dependent upon the vibration of the surface of the eye;

means for transmitting such second light wave having a fixed phase delay to a light detecting means; said light detecting means also receiving such reflected first light wave from such perturbated surface of the eye, such first and second light waves being merged at said light detecting means wherein the variation in phase delay between such first and second light waves will produce a moving fringe interference pattern;

means for processing such moving fringe interference pattern and creating an output signal; and means for displaying such output signal for viewing.

13. The tonometer of claim 12, wherein said light detecting means includes a Michaelson interferometer.

14. The tonometer of claim 12, wherein said light detecting means includes a Mach-Zehnder interferometer.

15. The tonometer of claim 12, wherein said first light wave and said second light wave are produced by splitting a single light wave and are monochromatic, wherein when such reflected first light wave is merged with such second light wave at said light detecting means, the distinct phases and polarization of such two light waves are superimposed to produce such moving fringe interference pattern.

* * * * *